US00PP21816P2

(12) United States Plant Patent
Carruth

(10) Patent No.: US PP21,816 P2
(45) Date of Patent: Mar. 29, 2011

(54) HYBRID TEA ROSE PLANT NAMED 'WEKSIAMIA'

(50) Latin Name: *Rosa hybrida*
Varietal Denomination: WEKsiamia

(75) Inventor: Thomas F. Carruth, Altadena, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/592,028

(22) Filed: Nov. 18, 2009

(51) Int. Cl.
*A01H 5/00* (2006.01)

(52) U.S. Cl. ..... Plt./130

(58) Field of Classification Search ..... Plt./130
See application file for complete search history.

*Primary Examiner*—Wendy Haas

(57) ABSTRACT

A new variety of Hybrid Tea rose suitable for garden decoration, having flowers of ruby red coloration.

1 Drawing Sheet

Classification: The present invention relates to a new *Rosa hybrida* plant.

Variety denomination: The new plant has the varietal denomination 'WEKsiamia'.

BACKGROUND OF THE INVENTION

This invention relates to a new and distinct variety of Hybrid Tea Rose. It has an undisseminated seedling of my creation as its seed parent with the following genetic origin ('City of San Francisco' (unpatented)×'Olympiad' (unpatented)) and has an undisseminated seedling of my creation as its pollen parent with the following genetic origin ['Amalia' (unpatented)×('Ingrid Bergman' (unpatented)×'All That Jazz' (unpatented))].

SUMMARY OF THE INVENTION

Among the features which distinguish the new variety from other presently available and commercial rose cultivars known to the inventor are the following combinations of characteristics: its red suffusion on the internal part of the anthers and filaments, its very large flowers and its mucronate leaf apice. The plant has an upright growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKsiamia' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, an undisseminated seedling of my creation by the following combination of characteristics: whereas 'WEKsiamia' bears very large sized (about 11.9 to about 18.3 cm. in diameter) double flowers (about 18 to 25 petals), the undisseminated seedling bears significantly smaller flowers (about 6.5 to about 9.0 cm. in diameter) with lesser petalage (about 11 to 16 petals). The new variety has an upright medium height growing habit (about 120 to about 155 cm. in height), whereas the seed parent has a significantly smaller rounded bushy growing habit (about 88 to about 105 cm. in height).

The new variety may be distinguished from its pollen parent, an undisseminated seedling of my creation by the following combination of characteristics: whereas 'WEKsiamia' bears double flowers (about 18 to 25 petals) of ruby red coloration, the undisseminated seedlings bears double flowers of brilliant orangey-red coloration with significantly heavier petalage (about 29 to 33 petals). The new variety has an upright medium height growing habit (about 120 to about 155 cm. in height), whereas the pollen parent has a bushy significantly taller growing habit.

COMPARISON WITH THE CLOSEST COMMERCIALLY AVAILABLE CULTIVAR

The new variety may be distinguished from its closest commercially available cultivar, 'WEKfrancoly' (U.S. Plant Pat. No. 19,373) by the following combination of characteristics: whereas 'WEKsiamia' bears double flowers (about 18 to 25 petals) of ruby red coloration, 'WEKfrancoly' bears double flowers of lasting red coloration sometimes with a green-white streak at the midrib of the outermost petals with significantly heavier petalage (about 27 to 32 petals). The new variety bears very large sized flowers (about 11.9 to about 18.3 cm. in diameter), whereas the closest commercially available cultivar bears significantly smaller range flower size (about 11 to about 15 cm. in diameter).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

FLOWER

The new variety usually bears its flowers singly. Flowers are borne on strong short to medium length stems (about 13 to about 65 cm.). Outdoors, the plant blooms abundantly and nearly continuously during the growing season. The flowers have a slight tea to spicy fragrance.

BUD

The peduncle is about 5.1 to about 7.2 cm. in length, of average to somewhat heavy caliper (about 0.2 to about 0.4 cm. in diameter), and usually erect and somewhat stiff. It is moderately rough, with some stipitate glands. Peduncle color is between 146B and 146A often lightly suffused, especially on the side exposed to the sun, with between 187B and 187A.

Before the calyx breaks, the bud is about 1.0 to about 1.8 cm. in diameter at the widest point, about 2.1 to about 3.1 cm. in length, and pointed in shape. The surface of the bud bears few foliaceous appendages, some hairs and many stipitate glands, usually with slender entire foliaceous parts extending beyond the tip of the bud about ½ or more of its length. Bud color is between 146A and 138A sometimes lightly suffused, especially on the side exposed to the sun, with between 187B and 187A.

The sepals are about 3.2 to about 4.4 cm. in length and about 0.9 to about 1.4 cm. in width at the widest point. The outer surface color of the sepal is between 146A and 138A sometimes lightly suffused, especially on the side exposed to the sun, with between 187B and 187A. The inner surface color of the sepal is near 137C broadly bordered by near 137A. After the sepals open, the inner surface color is often heavily suffused, especially on the area exposed to the sun, with between 187A and 187B. The inner surface of the sepal is covered with fine wooly tomentum; sepal margins are lined with some stipitate glands and hairs.

The receptacle of the flower is of short length (about 0.3 to about 0.5 cm.) and moderately thin in caliper (about 0.7 to about 0.9 cm. in diameter). The receptacle is cup-shaped in form. Its surface is very smooth with somewhat thin fleshy walls. The receptacle color is between 144A and 138A.

As the petals open (after the calyx breaks), the bud is about 1.9 to about 2.4 cm. in diameter at the widest point, about 3.2 to about 3.9 cm. in length, and moderately ovoid to pointed in form. The color of the under surfaces of the newly opened petals is between 59A and 46A sometimes heavily suffused near the petal edge with near 187A. At the point where the petal attaches, there is a very small zone of between 1C and 154C. The color of the upper surfaces of the newly opened petals is between 187B and 46A. At the point where the petal attaches, there is a small zone of between 13B and 12B.

BLOOM

When fully open, the bloom ranges from about 11.9 to about 18.3 cm. in diameter. Petalage is double with about 18 to 25 petals and about 2 to 6 petaloids irregularly arranged. When partially open, the bloom form is somewhat high centered to cupped, and the petals are loosely spiraled to cupped with petal edges slightly reflexed outward. When fully open, the bloom form is more cupped, and the petals are loosely cupped to moderately undulated with petal edges somewhat reflexed outward.

PETALS

The substance of the petals is moderately heavy and of medium thickness, with upper surfaces slightly satiny and under surfaces moderately shiny. The petals are about 4.6 to about 8.7 cm. in length and about 3.7 to about 8.3 cm. in width at the widest point. Petal margins are entire.

The outer petals are nearly round to somewhat obovate in shape with rounded apices.

The inner petals are moderately obovate in shape with rounded apices.

Petaloids are about 0.5 to about 4.0 cm. in length and about 0.4 to about 3.4 cm. in width at the widest point. Petaloids are irregularly shaped somewhat obovate with rounded apices.

NEWLY OPENED FLOWER

The under surface color of the outer, intermediate and inner petals is between 53C and 46B. At the point where the petal attaches, there is a very small zone of between 3C and 4B. The upper surface color of the outer, intermediate and inner petals is between 45A and 42A sometimes lightly blushed toward the petal edge with between 187A and 187B. At the point where the petal attaches, there is a small zone of between 13B and 12B.

The under and upper surface colors of the petaloids are similar in coloration to the upper and under surfaces of the intermediate and inner petals.

The general tonality of the newly opened flower is between 45A and 42A sometimes lightly blushed toward the petal edge with between 187A and 187B.

THREE-DAY-OLD FLOWER

The under surface color of the outer, intermediate and inner petals is between 60D and 46C. At the point where the petal attaches, there is a very small zone of between 4D and 2D. The upper surface color of the outer, intermediate and inner petals is between 53C and 46C. At the point where the petal attaches, there is a small zone of between 10D and 11C.

The under and upper surface colors of the petaloids are similar in coloration to the upper and under surfaces of the intermediate and inner petals.

The general tonality of the three-day-old flower is between 53C and 46C.

On the spent bloom, the petals usually drop off cleanly.

In October in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 125) and are arranged regularly about the pistils; a few are mixed with petaloids. The filaments are of medium length (about 0.4 to about 1.0 cm.) most with anthers. Filaments are between 3B and 2B in color usually heavily suffused with between 53B and 53C. The anthers are moderately large for the class and all open approximately at the same time. Anther color when immature is near 22B on the external part and near 11D on the internal part often moderately suffused with between 59C and 60B. Anther color at maturity is near 161C on the external part and near 200B on the internal part. Pollen is moderately abundant and between 11B and 12D in color.

FEMALE REPRODUCTIVE ORGANS

Pistils vary in number (average about 80). The styles are moderately even, somewhat long in length (about 0.8 to about 1.2 cm.), average in caliper, and loosely separated. Stigma color is between 9C and 8B. Style color is between 154C and 1C often moderately suffused with near 53B. Ovaries are usually all enclosed in the calyx.

Hips have not been observed on this variety when grown in Pomona, Calif.

FOLIAGE

The compound leaves are usually comprised of three to seven leaflets and are borne abundantly. The five-leaflet leaves are about 9.2 to about 15.6 cm. in length and about 8.3 to about 11.8 cm. in width at the widest point, moderately heavy to crisp in texture, and moderately glossy in finish on the upper side and matte in finish on the under side. The terminal leaflets are about 4.4 to about 6.4 cm. in length and about 3.6 to about 5.6 cm. in width at the widest point, shaped moderately ovate with mucronate apices and rounded bases. Their margins are usually simply serrate.

The upper surface color of the mature leaf is between 147A and 137A. The under surface color of the mature leaf is between 147B and 139B. The upper surface color of the young leaf is between 137A and 139B, often heavily suffused with between 187A and 183A. The under surface color of the young leaf is between 139C and 138B, often heavily suffused with between 187B and 183A.

The rachis is moderately heavy in caliper and rough. The upper side is deeply grooved with some hairs and stipitate glands on the edges of the grooves. The under side of the rachis is rough with few stipitate glands and small prickles. The rachis color is near 146C on the under side and near 137A on the upper side often heavily suffused, especially on the young leaves, with between 187B and 183A.

The stipules are about 1.0 to about 2.0 cm. in length and moderately wide (about 0.5 to about 0.8 cm.) with somewhat short straight points that usually turn out at an angle of more than 45 degrees and sometimes recurve toward the stem. The stipule color is between 137A and 138A sometimes moderately suffused, especially on the young leaves, with between 187B and 183A.

The petiole is moderately heavy in caliper and rough. The upper side is deeply grooved with some hairs and stipitate glands on the edges of the grooves. The under side of the petiole is rough with few stipitate glands and small prickles. The petiole is about 0.9 to about 1.6 cm. in length and about 0.1 to about 0.2 cm in diameter at the widest point. The petiole color is near 146C on the under side and near 137A on the upper side often heavily suffused, especially on the young leaves, with between 187B and 183A.

The plant displays an average degree of resistance to powdery mildew and rust as compared to other commercial varieties grown under comparable conditions in Pomona, Calif. The plant's winter hardiness and drought/heat tolerance are yet to be determined.

GROWTH

The plant has an upright medium height growing habit (about 120 to about 155 cm. in height and about 52 to about 62 cm. spread at the widest point), with moderately full branching. It displays vigorous growth and the canes are of medium to somewhat heavy caliper for the class (about 1.4 to about 1.8 cm. in width at the widest point).

The color of the major stems is between 146A and 146B. They bear some large prickles that are about 0.6 to about 0.9 cm. in length. The large prickles are hooked moderately downward with a very long broad oval base; prickle color is between 177B and 166C. The major stem bears few small prickles of similar shape and coloration.

The color of the branches is between 137C and 139B. They bear some large prickles which are of similar size and shape to the large prickles on the major stems; prickle color is between 1C and 160A. The branches bear few small prickles of similar shape and coloration.

The color of the new shoots is between 146C and 139B often heavily suffused with between 187B and 183A. They bear some large prickles which are of similar size and shape to the large prickles on the major stems; prickle color is between 1C and 160A often moderately suffused with between 187C and 187D. The shoots bear few small prickles of similar shape and coloration.

I claim:

1. A new and distinct Hybrid Tea rose plant of the variety substantially as described and illustrated herein.

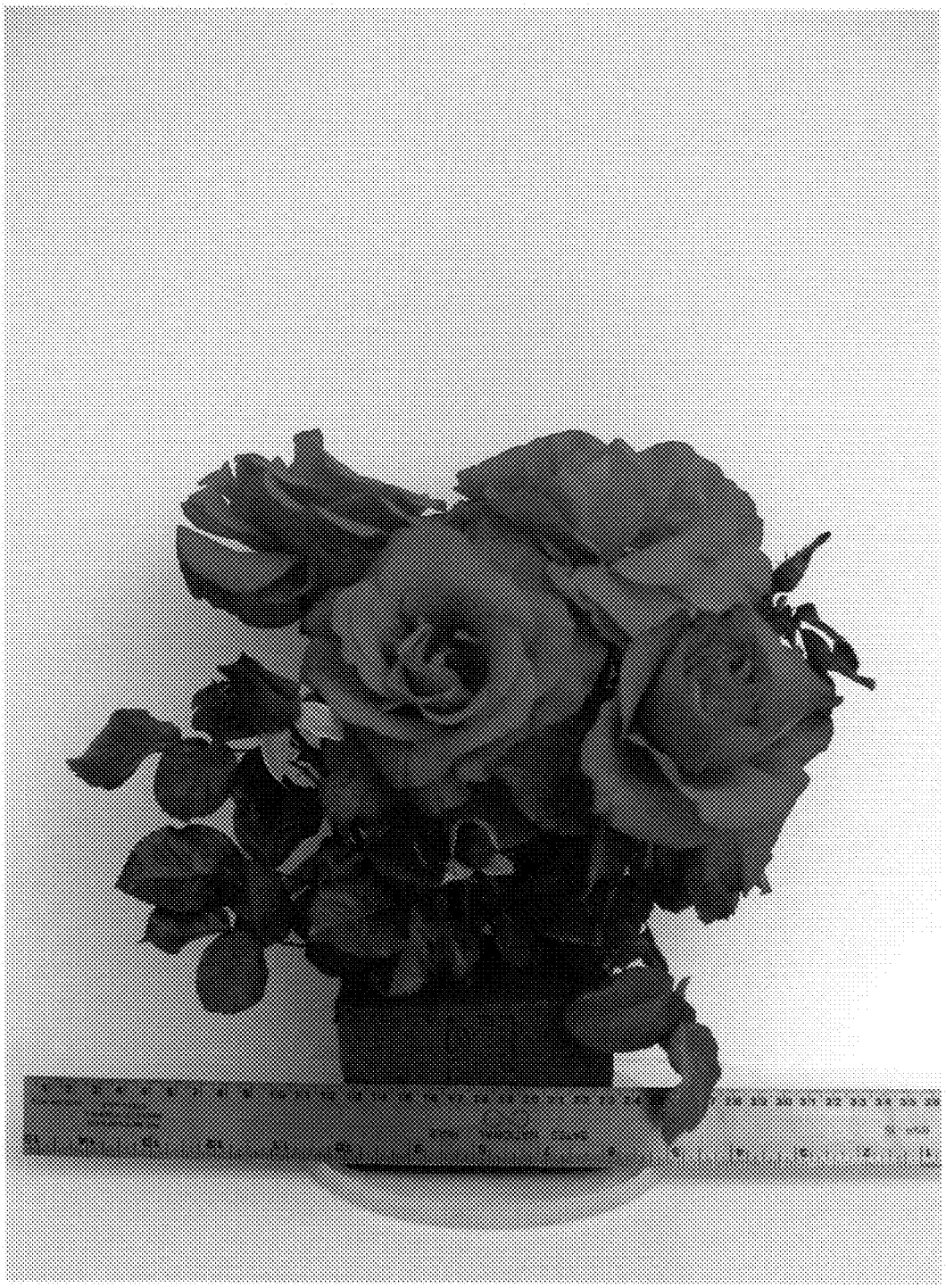

* * * * *